(12) United States Patent
Yi et al.

(10) Patent No.: US 7,186,215 B2
(45) Date of Patent: Mar. 6, 2007

(54) LIFTING TOOL FOR SURGICAL RETRACTORS

(76) Inventors: James Yi, 602 Hampton Rd., Clarks Summit, PA (US) 18411; Jay Taub, 1277 Ruffner Rd., Niskayuna, NY (US) 12309

( * ) Notice: Subject to any disclaimer, the term of this patent is extended or adjusted under 35 U.S.C. 154(b) by 498 days.

(21) Appl. No.: 10/602,522

(22) Filed: Jun. 24, 2003

(65) Prior Publication Data

US 2004/0092797 A1    May 13, 2004

Related U.S. Application Data

(60) Provisional application No. 60/391,002, filed on Jun. 24, 2002.

(51) Int. Cl.
*A61B 17/02* (2006.01)
(52) U.S. Cl. .................................................. 600/210
(58) Field of Classification Search ................ 600/210, 600/201, 213–217, 219, 228, 231, 232, 235; 606/86, 90, 105; D24/135
See application file for complete search history.

(56) References Cited

U.S. PATENT DOCUMENTS

| | | | |
|---|---|---|---|
| 3,089,211 A * | 5/1963 | Perusse | 24/556 |
| 3,168,093 A * | 2/1965 | Gauthier | 600/232 |
| 4,616,633 A * | 10/1986 | Vargas Garcia | 600/206 |
| 4,852,552 A | 8/1989 | Chaux | |
| 4,865,019 A | 9/1989 | Phillips | |
| 5,025,779 A | 6/1991 | Bugge | |
| 5,846,194 A | 12/1998 | Wasson et al. | |
| 5,879,291 A | 3/1999 | Kolata et al. | |
| 5,897,490 A | 4/1999 | Fox et al. | |
| 5,908,382 A | 6/1999 | Koros et al. | |
| 5,967,974 A | 10/1999 | Nicholas et al. | |
| 5,984,867 A | 11/1999 | Deckman et al. | |
| 6,033,425 A | 3/2000 | Looney et al. | |
| D425,620 S | 5/2000 | Koros et al. | |
| 6,113,535 A | 9/2000 | Fox et al. | |
| 6,159,231 A | 12/2000 | Looney et al. | |

* cited by examiner

*Primary Examiner*—Eduardo C. Robert
*Assistant Examiner*—David Comstock
(74) *Attorney, Agent, or Firm*—Thomas C. Saitta

(57) ABSTRACT

A lifting tool for use with a standard rib or chest retractor device where the tool acts to obliquely lift and spread open an incision, the chest wall and ribs, the tool having a pair of extended hook members disposed generally parallel and co-planarly on a mounting flange member.

19 Claims, 6 Drawing Sheets

LIFTING TOOL FOR SURGICAL RETRACTORS

This application claims the benefit of U.S. Provisional Patent Application Ser. No. 60/391,002, filed Jun. 24, 2002.

BACKGROUND OF THE INVENTION

This invention relates generally to the field of surgical devices known as rib, chest or sternal retractors, which are used to spread open an incision in the chest cavity and to separate the ribs of the patient to provide a larger access opening and greater visual field for the surgeon to perform medical procedures within the chest cavity, and more particularly to such devices having a design or structure to lift or raise one side of the incision and ribs relative to the other side of the incision and ribs such that accessibility and visibility are increased even further.

Rib or chest retractors, also known as internal mammary artery (IMA) retractors are known in the surgical field. A typical chest retractor comprises an L-shaped member, the base of the "L" comprising a fixed arm having outwardly oriented hook members affixed thereto, the hook members sized and structured to retain one side of the chest wall and a rib when inserted into an incision formed in the chest wall. An adjustable arm is mounted perpendicularly on the frame or rack member of the "L" and parallel to the fixed arm, and spreader actuator means is provided such that the arm can be moved linearly along the frame member such that the distance between the adjustable arm and the fixed arm can be increased or decreased. Outwardly oriented hook members are also affixed to the adjustable arm, these hook members likewise sized and structured to retain the other side of the chest wall and a rib when inserted into the incision in the chest wall. The spreader actuator means for the retractor may comprise the combination of spaced indentations along one side of the frame member to create a toothed rack member and a ratchet mechanism incorporated into the arm structure, or other mechanisms for imparting a spreading force on the adjustable arm may be utilized.

For increased access and visibility within the chest cavity during surgery, it is beneficial if one side of the chest wall is lifted or raised. Various devices have been developed to address this desire. U.S. Pat. No. 6,159,231 to Looney et al. shows an apparatus wherein an external cable lifting means is attached to one side of the chest retractor in order to raise that side of the incision. Patents to Fox et al. (U.S. Pat. No. 6,113,535), Nicholas et al. (U.S. Pat. No. 5,967,974), Deckman et al. (U.S. Pat. No. 5,984,867), Koros et al. (U.S. Pat. No. 5,908,382), Wasson et al. (U.S. Pat. No. 5,846,194), and Phillips (U.S. Pat. No. 4,865,019) show devices which utilize a distinct elevator mechanism, typically a foot or leg member positioned on the patient's chest, which provides a means via a ratchet, threaded rod, or manual securing member to raise one side of the incision. These are all specialized devices which are used in place of standard chest retractors, and unlike the invention at hand require a second step to lift the incision after the first step of spreading the incision.

Patents to Bugge (U.S. Pat. No. 5,025,779) and Chaux (U.S. Pat. No. 4,852,552) disclose devices that are less complicated than the devices disclosed in the above referenced patents. The Bugge device has a plate on which is pivotally mounted a lever arm, to which the arm of a separating frame is connected. Once the incision has been spread apart, an adjusting screw is used to tilt the lever arm and frame away from the plate, thereby raising the hook portion and thus that side of the incision. As with the other devices, the Bugge device cannot be used with standard retractors. Furthermore, unlike the invention at hand, it also requires a second action (turning the screw) after the first action of spreading the incision.

The Chaux device operates generally in the same manner as a standard retractor, but the spreader arms are joined to a notched rack bar in a manner which allows them to be rotated about the longitudinal axis of each spreader arm, and then locked in fixed relation to the rack bar. According to the patent, as the incision is spread apart, the fact that the spreader arms have been fixed at angles other than 90 degrees to the rack bar causes one side of the incision to be raised. Again, this device cannot be used with standard retractors, and operates on a different principle to the invention at hand.

It is an object of this invention to provide a tool or accessory adapted for use in combination with standard surgical chest retractors, where the combination of the tool and the retractor results in a lifting retractor device which operates to spread or separate the ribs and chest wall incision to provide greater accessibility to and increased visibility within the interior of the chest cavity, whereby one side of the patient's chest is lifted relative to the other side of the patient's chest, such that separation occurs obliquely rather than just laterally. It is a further object to provide such a device wherein the lifting tool and the chest retractor is an integral device. It is a further object to provide such a device wherein the lifting tool is distinct from the chest retractor. It is a further object to provide such a device wherein the lifting tool performs the oblique lifting movement without recourse to externally mounted lift structures. It is a further object to provide such a device wherein the lifting tool is durable, reusable, easily sterilized, and simple in construction, manufacture and use.

SUMMARY OF THE INVENTION

The invention is a tool or accessory for use with a standard rib or chest retractor device, of the type well known in the industry, where the tool acts to obliquely lift and spread open an incision, the chest wall and ribs. A typical chest retractor comprises an L-shaped member, the base of the "L" comprising a fixed arm having outwardly oriented hook members affixed thereto, the hook members sized and structured to retain one side of the chest wall and a rib when inserted into an incision formed in the chest wall. An adjustable arm is mounted perpendicularly on the frame or rack member of the "L" and parallel to the fixed arm, and spreader actuator means is provided such that the arm can be moved linearly along the frame member such that the distance between the adjustable arm and the fixed arm can be increased or decreased. Outwardly oriented hook members are also affixed to the adjustable arm, these hook members likewise sized and structured to retain the other side of the chest wall and a rib when inserted into the incision in the chest wall. The spreader actuator means for the retractor may comprise the combination of spaced indentations along one side of the frame member to create a toothed rack member and a ratchet mechanism incorporated into the arm structure, or other mechanisms for imparting a spreading force on the adjustable arm may be utilized.

The lifting tool or accessory comprises preferably a pair of extended hook members disposed generally parallel and co-planarly on a mounting flange member. The positions of the hook members relative to the mounting flange member are preferably adjustable, with the hook members being affixed thereto by mechanical interlocks or fasteners, such that the length of and the space between the hook members can be adjusted. The hook members open toward the interior of the lifting tool and are several inches in length. The mounting flange member is joined in non-planar manner to an elevation wall member, which as shown comprises an upper wall member joined in a non-planar manner to a lower wall member. The elevation wall member is joined in non-planar manner to an inwardly extending foot member, and the foot member terminates in an upwardly extending edge flange member. The combination of the mounting flange member, elevation wall member, foot member and flange member form a generally C-shaped main body, wherein the mounting flange member and the attached hook members extend at about a 45 degree angle from the plane containing the foot member. Alternatively, the elevation wall member and the foot member may be formed as curved members. The hook members and the elevation wall member are each of greater length than either the mounting flange member or the foot member, such that a substantial gap exists between the free ends of the hook members and the flange member of the foot member.

To use the invention, the free ends of the hook members on the lifting tool are used to retain the side of the chest wall and rib normally retained by the hook members on the adjustable arm of the chest retractor, and the foot member of the lifting tool is placed onto the patient's chest away from the incision. The hook members on the adjustable arm of the chest retractor are disposed onto the mounting flange of the lifting tool between the lifting tool hook members, such that the frame member of the chest retractor extends at an upward angle from the patient's chest related to the height of the elevation wall member. As the spreader actuator means is engaged to separate the adjustable arm from the fixed arm, the angular and positional relationship of the lifting tool extended hook members and the foot member results in an oblique separation of the chest wall and rib, such that the side of the incision retained by the lifting tool is raised upward and away from the chest cavity as the incision is broadened.

As alternative embodiments, the lifting tool hook members may by joined to the mounting flange in a non-adjustable and fixed orientation, the elevation wall member may be or planar, the foot member may be curved, the edge flange may be curved, or the lifting tool may be permanently joined to or be a component of the adjustable arm of the chest retractor.

DESCRIPTION OF THE INVENTION

With reference to the drawings, the invention will now be described in detail with regard for the best mode and the preferred embodiment. In a most general sense, the invention is a lifting tool or accessory for use in surgical procedures where access into the chest cavity of a patient is accomplished by making an incision in the chest wall and using a chest or rib retractor or spreader device to maximize the area of the opening in the chest wall for optimum access and visibility. The lifting tool, either in conjunction with or as an integral part of the chest retractor, causes one side of the incision and chest wall to be lifted in a generally oblique upward direction away from the interior of the chest cavity such that greater separation is achieved between the chest wall and the internal organs than ordinarily achieved by chest retractors which only spread the incision laterally. For purposes of discussion herein, as a patient will usually lie horizontally on an operating table with the chest facing upward, the generally vertical direction upward and perpendicular from the table surface or the chest shall be taken as the vertical direction, and the direction perpendicular to the vertical direction or parallel to the table surface shall be taken as the lateral or horizontal direction when describing components of the invention. The oblique direction shall be taken as any direction between horizontal and vertical, such that an oblique lifting of one side of the chest wall means that the chest wall is raised in a rolling manner both vertically and laterally to increase accessibility and visibility by creating a large, oblique opening in the chest wall.

Figure 1:
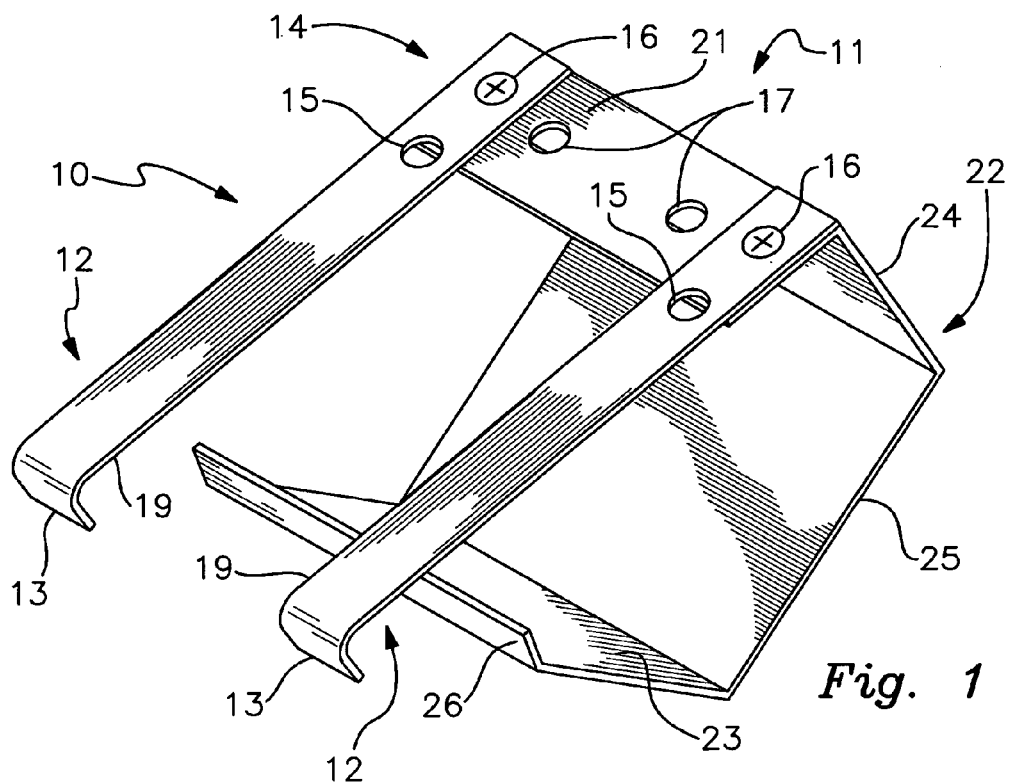
FIG. 1 is a perspective view of the lifting tool invention.
Figure 2:
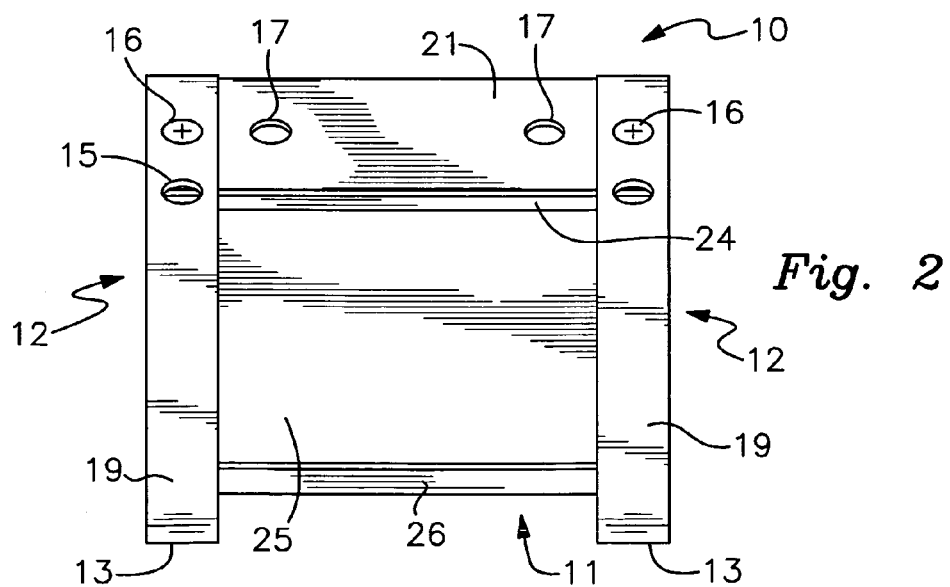
FIG. 2 is a front view of the lifting tool of FIG. 1.
Figure 3:
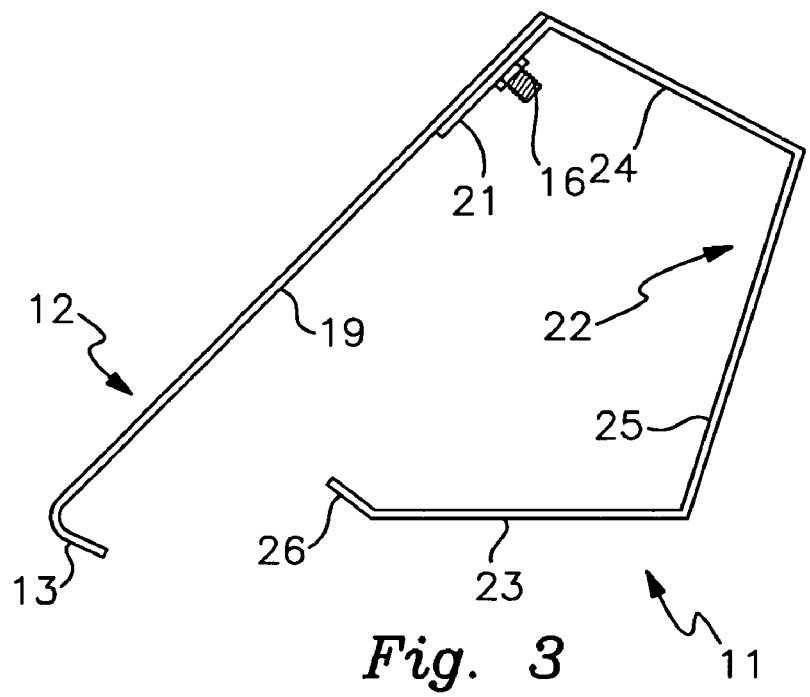
FIG. 3 is a side view of the lifting tool of FIG. 1.
Figure 11:
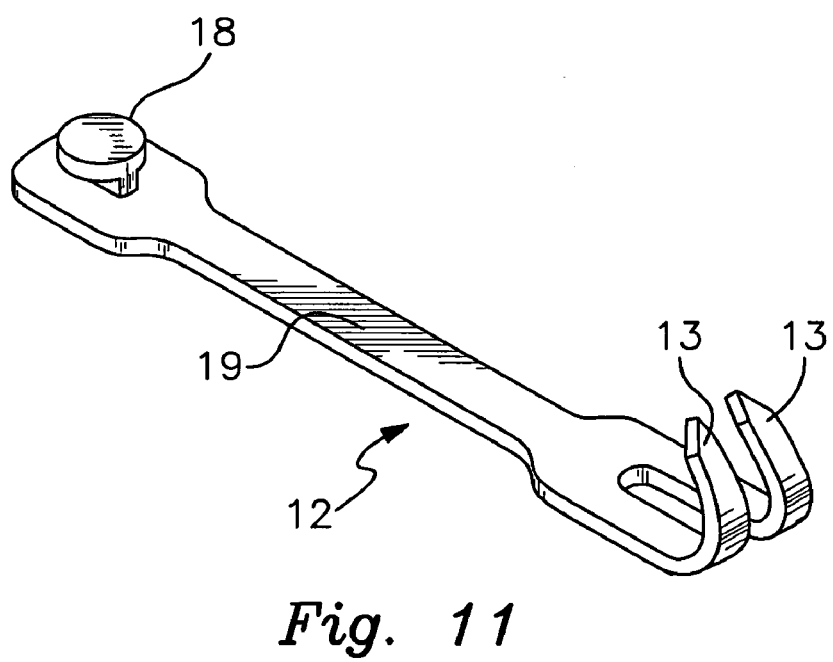
FIG. 11 is a perspective view of the preferred embodiment of the hook members used with the preferred alternative embodiment of the invention.
Figure 6:
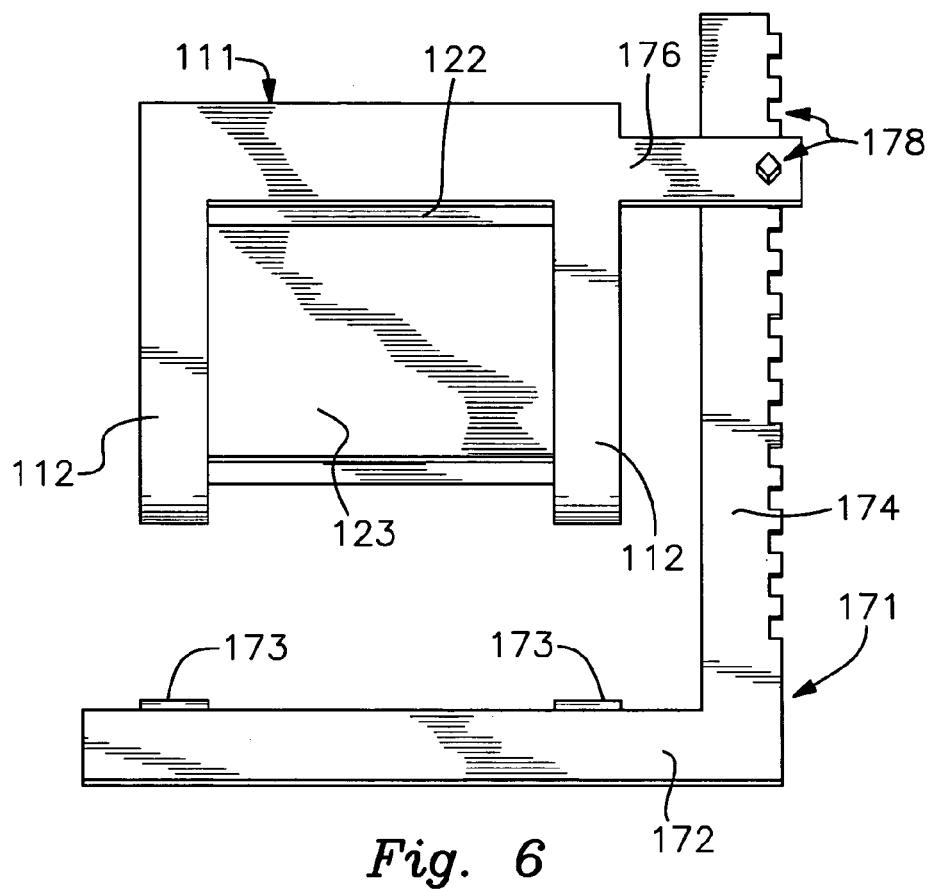
FIG. 6 is a front view of an alternative embodiment of the invention, showing the lifting tool and chest retractor structured as an integral unit.

With reference now to FIGS. 1 through 3, a first embodiment of the lifting tool or accessory 10 is shown. The lifting tool 10 comprises in general a main body 11 to which are attached at least one and most preferably a pair of extended hook members 12. The main body 11 is structured to be generally C-shaped in transverse cross-section, i.e., when viewed from the side, as shown in FIG. 3. The extended hook members 12 are mounted such that they extend downwardly across the opening of the "C". The extended hook members 12 are the members used to grasp one side of an incision 91 made in a chest wall 92 of a patient, such that the side of the chest wall 92 can be pulled to enlarge the incision 91. The distal or free ends of the body portion 19 of the extended hook members 12 are curved or folded to define hook ends 13 which are sized to receive and secure the chest wall 92 including the ribs 93. Preferably, hook positioning means 14 are provided such that the length and position of the extended hook members 12 can be altered relative to the main body 11. As shown in FIGS. 1 through 3, this may be accomplished for example by providing multiple apertures 15 and mechanical fasteners 16, such as threaded bolts and nuts, which secure the extended hook members 12 to apertures 17 provided in the main body 11. Alternatively, the apertures 15 in the extended hook members 12 could be extended to define slots to receive the mechanical fasteners 16, or the proximal ends of the hook members 12 could be provided with key or tab members 18, as shown in FIG. 11, insertable into the slots or apertures 17 provided on the main body 11, or other hook positioning means 14 structure may be utilized. Further alternatively, as shown in FIG. 6, the extended hook members 12 could be permanently attached to or formed as an integral part of the main body 11, in which case the extended hook members 12 would not be adjustable. The extended hook members 12 are adapted to be mounted in a generally parallel, spaced relationship adjacent the sides of the main body 11, but the extended hook members 12 of the embodiments having hook positioning means 14 can be disposed in a non-parallel manner to accommodate different patient anatomical conditions. Most preferably, the width of the hook members 12 is minimized by providing narrow intermediary portions in order to create more working space between the hook members 12.

Figure 7:
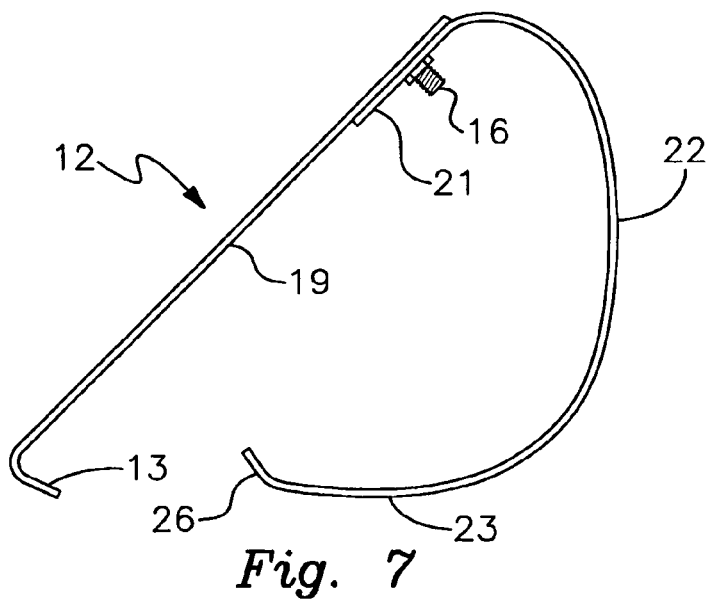
FIG. 7 is a side view of an alternative embodiment of the invention.

The main body 11 of lifting tool 10 is a rigid member able to withstand tensile or torsional forces without undue flexing or bending, and is preferably formed of stainless steel or like material able to be sterilized and re-used. The main body 11 comprises a mounting flange member 21 joined to an elevation wall member 22 and a foot member 23 to define a generally C-shaped configuration. The mounting flange member 21 receives the extended hook members 12, and is most preferably planar. The elevation wall member 22 joins the mounting flange member 21 to the foot member 23, the foot member 23 being the major portion of the main body 11 which rests on and contacts the patient's chest externally during the surgical procedure. The foot member 23 is preferably planar, but may be formed with some curvature as shown in FIG. 7. The structure of the main body 11 is such that the extended hook members 12 and mounting flange member 21 extend outwardly from the open side of C-shaped main body 11, and are disposed at an oblique angle to the plane containing the foot member 23, and most preferably at an angle of about 45 degrees. In other words, the extended hook members 12 extend outward and downward at about 45 degrees from vertical, or from a line taken perpendicularly to the plane containing the foot member 23. The length of the extended hook members 12 is such that the hook ends 13 will be positioned even with or preferably slightly beyond and below the plane containing the foot member 23.

It is most preferred that the elevation wall member 22 extend outward in the direction away from the extended hook members 12, which may be accomplished by curving the elevation wall member 22, but is preferably accomplished by structuring elevation wall member 22 to comprise a preferably planar upper wall member 24 and a preferably planar lower wall member 25 joined at an acute angle. In this embodiment the upper wall member 24 will be angularly joined to the mounting flange member 21 and the lower wall member 25 will be angularly joined to the foot member 23. The outwardly extending structure of elevation wall member 22 increases the pivoting or rocking directional movement when force is applied along the plane containing the extended hook members 12 and mounting flange 21.

Figure 8:
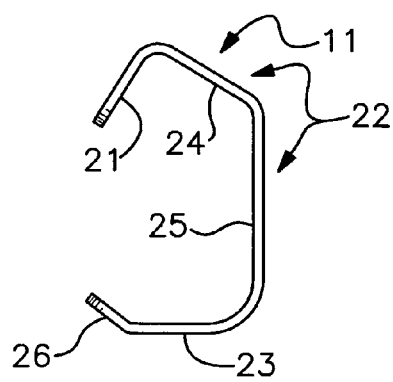
FIG. 8 is a side view of a preferred alternative embodiment of the invention.
Figure 9:
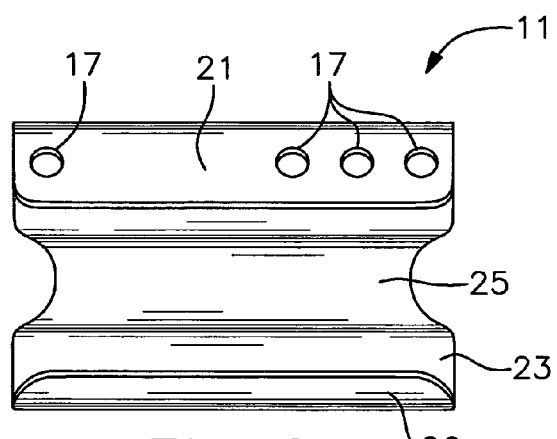
FIG. 9 is a front view of the preferred alternative embodiment of the invention.
Figure 10:
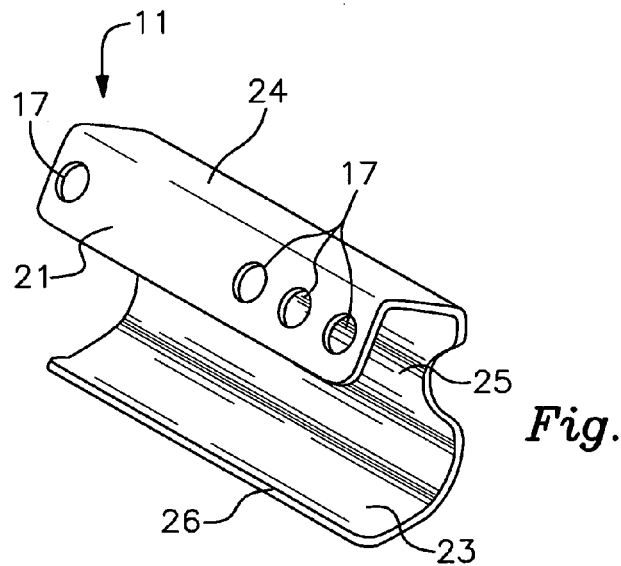
FIG. 10 is a perspective view of the preferred alternative embodiment of the invention.

It is also preferred that the edge of the foot member 23 facing the extended hook members 12 be rolled, beveled, formed into or joined to edge flange member 26 without a sharp edge or corner, with edge flange member 26 angled slightly upward. In this manner a narrow edge is not presented directly in contact with the patient's skin during use. It is also preferred, as shown in FIGS. 8 through 10, which illustrate the more preferred embodiment of the invention, that each of mounting flange member 21, upper wall member 24, lower wall member 25, foot member 23 and edge flange member 26 be joined to respective adjacent members by a radiused or curved junction.

The most preferred structure has a mounting flange member 21 with a planar portion of about 1.01 inches joined to an upper wall member 24 with a planar portion of about 1.16 inches at an interior angle of about 90 degrees with a radius of about 0.125 inches. Upper wall member 24 is joined to a lower wall member 25 with a planar portion of about 1.84 inches at an interior angle of about 122 degrees with a radius of about 0.125 inches. Lower wall member 25 is joined to a foot member 23 with a planar portion of about 0.72 inches at an interior angle of about 90 degrees with a radius of about 0.625 inches. Foot member 23 is joined to an edge flange member 26 with a planar portion of about 0.54 inches at an angle of about 140 degrees with a radius of about 0.125 inches. In this configuration, the mounting flange member 21 extends downwardly at an angle of about 32 degrees from vertical, based on foot member 23 defining horizontal. This configuration produces a main body 11 with a height of about 3.5 inches as measured with the foot member 23 disposed on a horizontal surface. The preferred thickness of the main body 11 is about 0.12 inches and the preferred width is about 5.25 inches.

Figure 4:
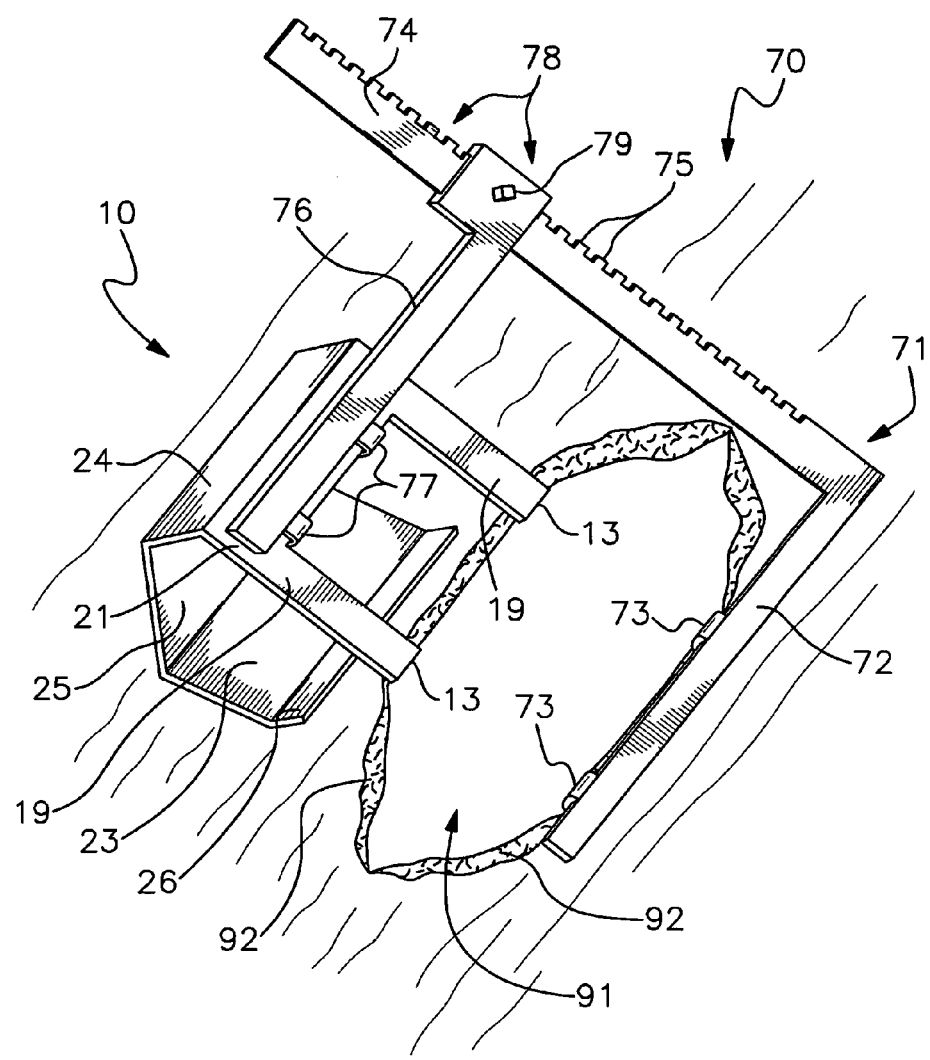
FIG. 4 is a perspective view of an alternative embodiment of the lifting tool in use with a chest retractor.
Figure 5:
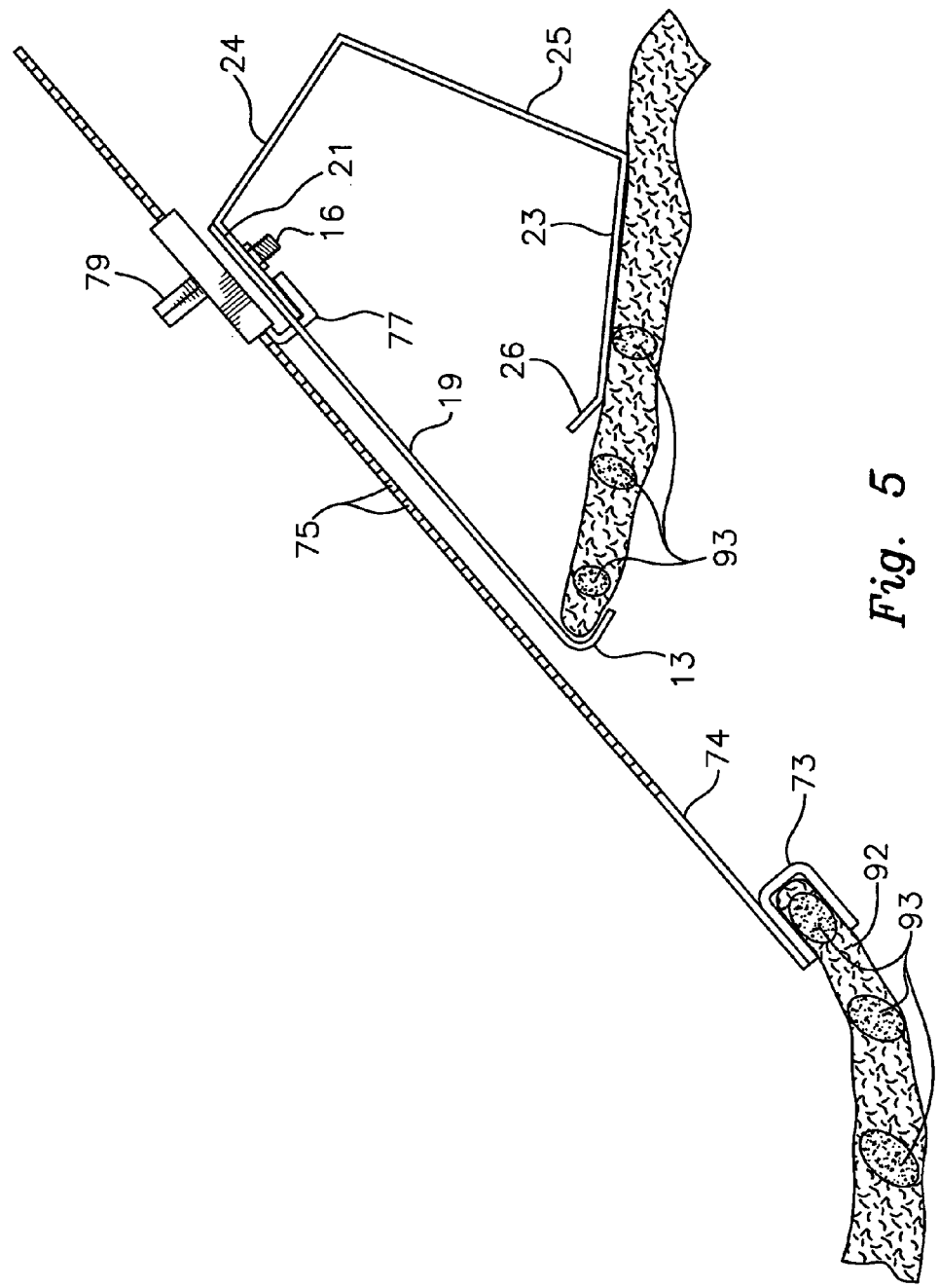
FIG. 5 is a side view of the lifting tool of FIG. 1 in use in combination with a chest retractor with the chest wall shown in cross-section.

The lifting tool 10 is used in conjunction with a standard chest retractor 70 comprising a generally L-shaped main body member 71, as shown in FIGS. 4 through 6. The base of the main body 71 comprises a fixed arm member 72 to which are affixed two retractor hook members 73, with the retractor hook members 73 extending below the fixed arm member 72 and opening to the outside of the retractor 70. The retractor hook members 73 are sized to retain and secure one side of the incision 91 and chest wall 92, including ribs 93. The fixed arm member 72 is typically perpendicularly joined to a frame or rack member 74 having a series of teeth members 75 arrayed along the outer edge. An adjustable arm member 76 is connected perpendicularly to the rack member 74 and parallel to the fixed arm member 72, in such a manner that the distance between the adjustable arm member 76 and the fixed arm member 72 can be varied using spreader actuation or retraction means 78, which as shown may comprise a ratchet mechanism 79 in combination with the teeth members 75. Two retractor arm hook members 77 are affixed below the adjustable arm member 72, these arm hook members 77 likewise sized to retain and secure one side of the incision 91 and chest wall 92, including ribs 93, and opening to the outside of the retractor 70. Such chest retractors 70 are well known in the art. The lifting tool 10 is able to be utilized with various other chest retractor structures where a pair of generally parallel arms can be separated by an actuation mechanism. The typical method for using the chest retractor 70 is to first cut an incision opening 91 in the chest. The opposing sets of retractor hook members 73 and arm hook members 77 are then inserted into the opening to retain the opposite sides of the chest wall 92. The spreader actuation means 78 is then initiated by the surgeon to move the adjustable arm member 76 outward along the rack member 74 to increase the distance between the fixed arm member 72 and the adjustable arm member 76, thereby spreading the chest wall 92 to create a larger opening.

To utilize the lifting tool 10, only the retractor hook members 73 on the fixed arm member 72 are placed into the incision 91. The hook ends 13 of the extended hook members 12 on the lifting tool 10 are inserted into the other side of the incision 91, such that the foot member 23 rests atop the patient's chest adjacent or near to the incision 91. Thus the retractor hook members 73 and the lifting tool hook ends 13 face in opposite directions and retain opposite sides of the chest wall 92. The adjustable arm member 76 of the chest retractor 70 is separated from the fixed arm member 72 a distance such that the arm hook members 77 on the retractor adjustable arm member 76 abut and retain the edge of the mounting flange member 21 of the lifting tool 10, with the retractor hook members 73 disposed between the extended hook members 12, as shown in FIGS. 4 and 5. In this passive position prior to the spreading of the incision 91, the chest retractor 70 is angled obliquely upward from the chest, rather than lying in a horizontal position. As the spreader actuation means 78 is further used to move the adjustable arm member 76 away from the fixed arm member 72, the relative movement causes the mounting flange member 21 and extended hook members 12 to be pushed away from the fixed arm member 72. As the upper portion of the lifting tool 10 is pushed away from the retractor fixed arm member 72, the angular disposition relative to the foot member 23 causes the lifting tool 10 to pivot or rotate, such that the hook ends 13 are lifted obliquely upward. This causes the chest wall 92 retained by the hook ends 13 to be raised vertically at the incision 91 is spread open, such that the chest wall 92 on the side of the lifting tool 10 is shifted both laterally to open the incision 91 and vertically to separate the chest wall 92 from the internal organs.

As set forth above, the main embodiment of the invention is the lifting tool 10 as used in combination with a separate chest retractor 70. However, in an alternative embodiment as shown in FIG. 6, the invention may comprise an integral device comprising an L-shaped body member 171 with a fixed arm member 172 having hook members 173 which is joined to a rack member 174, spreader actuation means 178, and an adjustable arm member 176 comprising extended hook members 112 and a main body 111 comprising a foot member 123 and an elevation wall member 122, configured in similar manner to the lifting tool 10 as previously described.

We claim:

1. A lifting tool adapted for use in combination with a chest retractor to separate and lift one side of an incision in a chest cavity to provide greater access and visibility to a surgeon, comprising:
a main body having a generally C-shaped configuration, said main body comprising a foot member, an elevation wall member joined to said foot member, an edge flange member joined to said foot member, and a mounting flange member joined to said elevation wall member;
wherein said elevation wall member comprises an upper wall member joined to a lower wall member, said upper wall member being joined to said mounting flange member and said lower wall member being joined to said foot member; and
a pair of extended hook members mounted to said mounting flange member, each of said extended hook members comprising a hook end and a body portion;
wherein said edge flange is joined to said foot member at an interior angle of about 140 degrees, said foot member is joined to said lower wall member at an internal angle of about 90 degrees, said lower wall member is joined to said upper wall member at an internal angle of about 122 degrees, and said upper wall member is joined to said mounting flange member at an interior angle of about 90 degrees.

2. The tool of claim 1, wherein said extended hook members are adjustably mounted to said mounting flange member.

3. The tool of claim 2, wherein said extended hook members are adjustably mounted to said mounting flange member by positioning means comprising apertures and tab members.

4. The tool of claim 2, wherein said extended hook members are adjustably mounted to said mounting flange member by positioning means comprising apertures and mechanical fasteners.

5. The tool of claim 1, wherein said edge flange has a planar portion of about 1.01 inches, said upper wall member has a planar portion of about 1.16 inches, said lower wall member has a planar portion of about 1.84 inches, said foot member has a planar portion of about 0.72 inches, and said edge flange member has a planar portion of about 0.54 inches.

6. The tool of claim 1, wherein with said foot member defining horizontal said mounting flange member is disposed at an angle of about 32 degrees from vertical.

7. The tool of claim 1, wherein said foot member is joined to said elevation wall member along a radiused junction.

8. The tool of claim 1, wherein said edge member is joined to said foot member along a radiused junction.

9. The tool of claim 1, further comprising a chest retractor comprising a generally L-shaped main body member comprising a fixed arm member and a pair of retractor hook members connected thereto, and a rack member joined to said fixed arm member,
wherein said lifting tool main body is joined to said rack member in a manner allowing the distance between said fixed arm member and said lifting tool main body to be varied.

10. A lifting tool adapted for use in combination with a chest retractor to separate and lift one side of an incision in a chest cavity to provide greater access and visibility to a surgeon, comprising:
a main body having a generally C-shaped configuration, said main body comprising a foot member, an elevation wall member joined to said foot member, and a mounting flange member joined to said elevation wall member; and
a pair of extended hook members mounted to said mounting flange member, each of said extended hook members comprising a hook end and a body portion;
and further comprising a chest retractor comprising a generally L-shaped main body member comprising a fixed arm member and a pair of retractor hook members connected thereto, a rack member joined to said fixed arm member, and an adjustable arm member joined to said rack member in a manner allowing the distance between said fixed arm member and said adjustable arm member to be varied, with a pair of arm hook members attached to said adjustable arm member;
wherein said arm hook members of said adjustable arm member are positioned on said mounting flange member between said extended hook members.

11. The tool of claim 10, wherein said main body further comprises an edge flange member joined to said foot member.

12. The tool of claim 11, wherein said elevation wall member comprises an upper wall member joined to a lower wall member, said upper wall member being joined to said mounting flange member and said lower wall member being joined to said foot member.

13. The tool of claim 10, wherein said elevation wall member comprises an upper wall member joined to a lower wall member, said upper wall member being joined to said mounting flange member and said lower wall member being joined to said foot member.

14. The tool of claim 10, wherein said extended hook members are adjustably mounted to said mounting flange member.

15. The tool of claim 14, wherein said extended hook members are adjustably mounted to said mounting flange member by positioning means comprising apertures and tab members.

16. The tool of claim 14, wherein said extended hook members are adjustably mounted to said mounting flange member by positioning means comprising apertures and mechanical fasteners.

17. The tool of claim 10, wherein said foot member is joined to said elevation wall member along a radiused junction.

18. The tool of claim 10, wherein said edge member is joined to said foot member along a radiused junction.

19. A method of separating and lifting one side of an incision in a chest wall to provide greater access and visibility to a surgeon, comprising the steps of:

providing a lifting tool comprising a main body having a generally C-shaped configuration, said main body comprising a foot member, an elevation wall member joined to said foot member, and a mounting flange member joined to said elevation wall member, and a pair of extended hook members mounted to said mounting flange member, each of said extended hook members comprising a hook end and a body portion;

providing a chest retractor comprising a generally L-shaped main body member comprising a fixed arm member and a pair of retractor hook members connected thereto, a rack member joined to said fixed arm member, and an adjustable arm member joined to said rack member in a manner allowing the distance between said fixed arm member and said adjustable arm member to be varied, with a pair of arm hook members attached to said adjustable arm member;

positioning said fixed arm hook members on one side of an incision in a chest wall so as to retain one side of the chest wall;

positioning said foot member of said main body on said chest wall adjacent the other side of said incision and positioning said hook ends of said main body of said lifting tool on the other side of said incision in said chest cavity so as to retain the other side of the chest wall;

positioning said arm hook members of said adjustable arm member on said mounting flange member between said extended hook members; and increasing the distance between said fixed arm member and said adjustable arm member, thereby increasing the distance between said fixed arm member and said mounting flange member, and thereby widening said incision and lifting the other side of said chest wall.

* * * * *